United States Patent [19]

Proni et al.

[11] Patent Number: 4,631,483
[45] Date of Patent: Dec. 23, 1986

[54] PARTICLE ANALYZING APPARATUS AND METHOD OF MOVING PARTICLES IN SUSPENSION THROUGH SUCH APPARATUS

[75] Inventors: Oscar Proni, Hollywood; Bobby D. James, Hialeah, both of Fla.

[73] Assignee: Coulter Electronics, Inc., Hialeah, Fla.

[21] Appl. No.: 576,096

[22] Filed: Feb. 1, 1984

[51] Int. Cl.[4] ............................................. G01N 27/00
[52] U.S. Cl. ................................ 324/71.4; 73/864.11; 73/864.34; 141/67
[58] Field of Search ...................... 324/71.1, 71.4, 450; 417/472; 222/209; 141/5, 67; 73/864.11, 864.34; 418/153, 156; 377/10-12

[56] References Cited

U.S. PATENT DOCUMENTS

| | | | |
|---|---|---|---|
| 1,085,306 | 1/1914 | Steinbecker | 417/472 |
| 2,180,818 | 11/1939 | Fields et al. | 417/472 |
| 2,681,012 | 6/1954 | Hackman | 417/472 |
| 2,869,078 | 1/1959 | Coulter et al. | 324/71.1 |
| 3,299,354 | 1/1967 | Hogg | 324/450 |
| 3,654,439 | 4/1972 | Estelle et al. | 377/10 |
| 3,901,653 | 8/1975 | Jones et al. | 73/864.34 |
| 3,972,683 | 8/1976 | Lape | 73/864.11 |
| 4,080,832 | 3/1978 | Moody et al. | 73/864.34 |
| 4,303,337 | 12/1981 | James et al. | 356/72 |

FOREIGN PATENT DOCUMENTS 1025497  4/1980  Japan .

OTHER PUBLICATIONS

Robertshaw Controls Company, Knoxville, Tennessee, Bellows, Catalog R, Oct. 1982, p. 5.
Igor J. Karassik et al., McGraw-Hill Book Company, Pump Handbook, 1976, section 10.20, pp. 10-231 to 10-233.

Primary Examiner—Stewart J. Levy
Assistant Examiner—Kevin D. O'Shea
Attorney, Agent, or Firm—Gerald R. Hibnick; Carl Fissell, Jr.

[57] ABSTRACT

A particle analyzing apparatus and method of moving and counting particles in suspension through such an apparatus. The particle analyzing apparatus comprises a particle counting device wherein particles in suspension are caused to be moved through an aperture whose effective impedance is changed with the passage of each particle therethrough and a fluid connection means for drawing a quantity of the suspension through the aperture, including a source of vacuum. The source of vacuum comprises a bellows having an end, and a constant force means connected to the end of the bellows means.

10 Claims, 5 Drawing Figures

PARTICLE ANALYZING APPARATUS AND METHOD OF MOVING PARTICLES IN SUSPENSION THROUGH SUCH APPARATUS

BACKGROUND OF THE INVENTION

This invention relates to a particle analyzing device and a method of moving and counting particles in suspension through such a device. More particularly the invention relates to a source of vacuum for drawing a fluid sample, a quantity of a suspension of particles, through a particle counting device having an aperture whose effective impedance is changed with the passage of each particle through said aperture, which vacuum remains substantially constant during its operative cycle. The invention also concerns the repeated movement of the same volume of different fluid blood samples regardless of the altitude at which the device is operated and wherein the magnitude of the vacuum source is self-regulating in that the magnitude of the vacuum generated is only a function of altitude and more particularly the force of gravity. Such a device furthermore repeatedly moves the same volume of different fluid samples in the same interval of time, or operative cycle, at any given altitude and stroke length and wherein said time interval is only a function of altitude. Such a device can also function as an aperture blockage indicator by comparing the actual time interval between the initiation and end of an operative cycle and a known correct time interval at any given altitude thereby obviating the use of a separate optics viewer used to observe the aperture. Although the sample flow rate varies as a function of altitude, since the counting time interval utilized for devices constructed in accordance with this invention is fixed, it is a simple matter of calibration to compensate for such factor. This device which does not utilize a manometer system having a mercury column used as a constant vacuum source or pressure indicator obviates the problems associated with the use of such a toxic substance and is independent of atmospheric variations which affect such a mercury column. Furthermore, since it is manually actuated by an operator, no pumps, electrical power, or other motive power is required to operate its vacuum source and due to its simple design, it is inexpensive to manufacture. Additionally, since the source of the vacuum's driving force is the force of gravity, the driving force does not suffer from any of the problems that are associated with other forces, including temperature, stretching, aging, repeatability, breaking, cracking, and the like.

Furthermore, since the vacuum source operates without any sliding contact during its operative cycle, the problems associated with mechanical friction are totally eliminated thereby resulting in the achievement of high repeatability over long periods of time.

Also since the vacuum remains substantially constant, the necessity of providing an indicator to monitor its pressure is obviated. Furthermore, since the device does not require a continuously generated vacuum, attendant vacuum bottles and supporting hardware are unnecessary.

Manually operative particle analyzing device having a vacuum source which remains substantially constant during its operative cycle are known as shown in U.S. Pat. No. 2,869,078, Fluid Metering Apparatus, issued Jan. 13, 1959 to Coulter et al. Coulter describes the importance of providing "a precise and accurate metering of a predetermined and constant volume of fluid to be tested as it passes the scanning point of a detecting system" (column 1, line 70 to column 2, line 3). This is achieved by utilizing a "manometer system having a mercury column . . . to achieve a substantially unchanging pressure differential in the system during the metering cycle" (column 2, line 20 to line 24). This device suffers from the obvious drawbacks inherent in utilizing such a toxic substance, mercury, as a component of the vacuum source.

A particle counting apparatus which utilizes a suction pump and flow regulator to provide a vacuum source whereby a uniform flow rate is achieved is taught by U.S. Pat. No. 3,654,439, Particle Counting Apparatus Having Automatic Display And Threshold Setting, issued Apr. 4, 1972 to Estelle et al. The pump believed to be utilized was a conventional "fish tank" Bellowfram ® type vacuum pump with a flow regulator, the latter to maintain the vacuum constant. Such a combined vacuum pump and regulator in addition to requiring electric power does not provide as constant a vacuum nor one which is continuously repeatable over time. Furthermore, devices utilizing such types of vacuum sources generally require that the regulator be finely adjusted by such means as a mercury manometer indicator which monitors the pressure of the vacuum source.

A particle counting apparatus which utilizes a vacuum source only during the portions of the operating cycle where vacuum is required and which requires no indicator is taught by U.S. Pat. No. 4,303,337, Apparatus For Detecting Hemoglobin And White Blood Cell Count In Blood, issued Dec. 1, 1981 to James et al. It utilizes an intermittently operable vacuum system, operatable only during the count cycle. This system utilizes a solenoid operated vacuum dispenser coupled to detecting upper and lower limit switches which function to establish operable vacuum limits during the count cycle and to operate an alarm to alert the operator to vacuum malfunctions; it does not provide as constant a vacuum. Since it is electrically powered, it does not have the same advantages as the manually operable device of the present invention as well as requiring electrical components to generate the vacuum which increases its cost. Not being driven by the force of gravity, it lacks the concomitent advantages thereof previously described.

SUMMARY OF THE INVENTION

The invention, in its broadest aspects, includes a particle analyzing apparatus and a method of moving and counting particles in suspension through such an apparatus. The particle analyzing apparatus, in its broadest aspects, comprises a particle counting device wherein particles in suspension are caused to be moved through an aperture whose effective impedance is changed with the passage of each particle therethrough and fluid connection means for drawing a quantity of said suspension through said aperture, including a source of vacuum. The source of vacuum comprises a bellows or flexible means having an end, and a force means, connected to said end of said bellows means.

The flexible means has a valved chamber that is contracted and expanded by pumping to force air through a nozzle and drawing said suspension toward said nozzle, said flexible means having axial flexibility and circumferential rigidity and having a low spring rate. In narrower aspects thereof the constant force means comprises a fixed weight and is freely driven by the force of gravity and the bellows means has a low spring rate.

DETAILED DESCRIPTION OF THE PREFERRED EMBODIMENT

Figure 1:
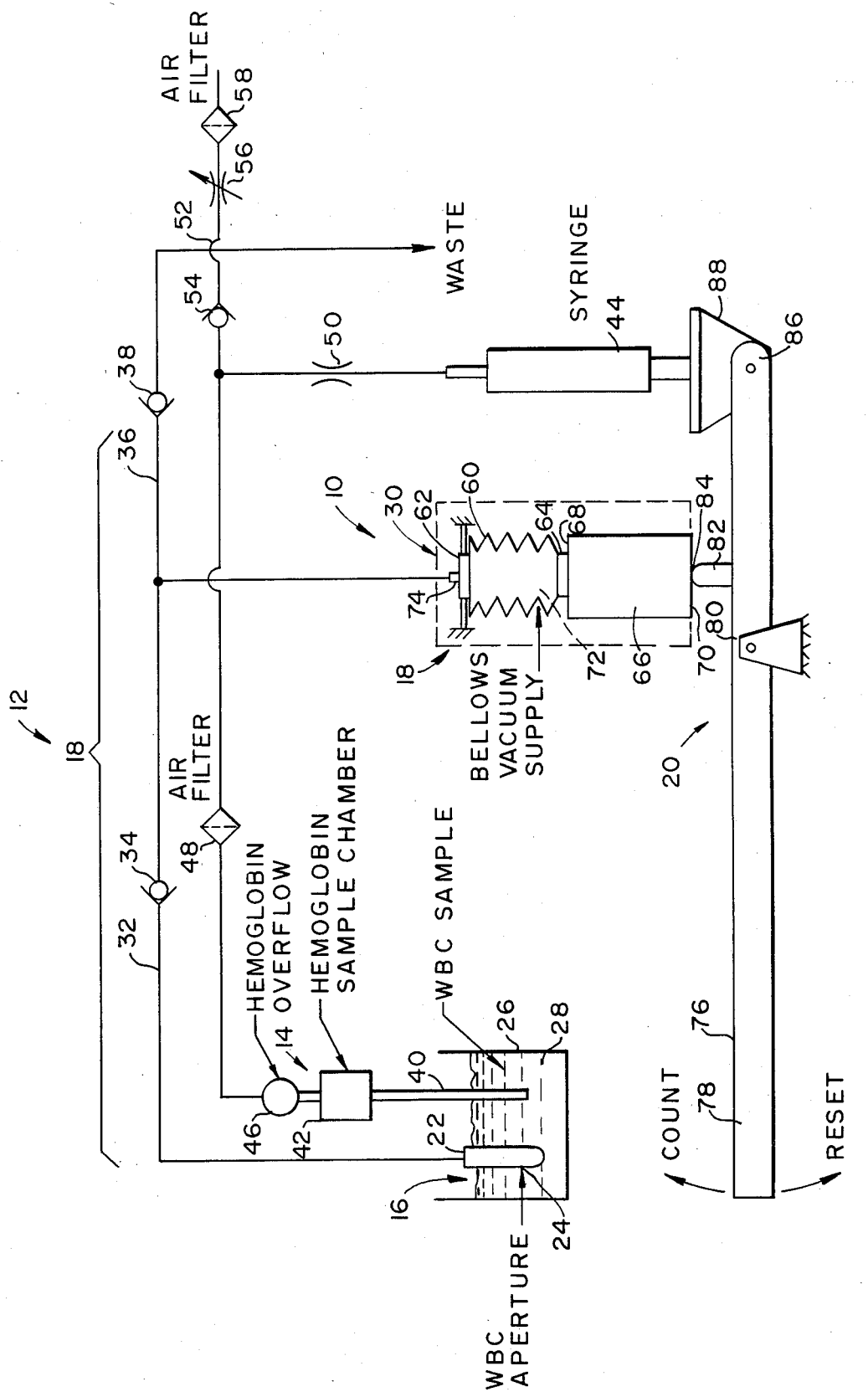
FIG. 1 is a schematic view of part of a quantitative semiautomated blood analyzer which includes both a hemoblobin measuring apparatus and the present invention, a particle analyzing apparatus.

Referring now to the drawings FIGS. 1-4, particularly to FIG. 1, a particle analyzing or studying apparatus or device, generally indicated by reference numeral 10, is constructed in accordance with the preferred embodiment of the invention which is part of a quantitative semiautomated blood analyzer, generally indicated by reference numeral 12, which further includes a hemoglobin measuring apparatus, generally indicated by reference numeral 14.

The particle analyzing apparatus 10 comprises a particle counting device 16 wherein particles in suspension are caused to be moved through an aperture therein whose effective impedance is changed with the passage of each particle therethrough, which device is coupled to fluid connection means, generally indicated by reference numeral 18, for drawing a quantity of said suspension through said aperture, and actuation means, generally indicated by reference numeral 20, for operating, simultaneously, said particle analyzing and hemoglobin measuring apparatuses 10 and 14, respectively.

The particle counting device 16 comprises a conventional Coulter type apparatus such as described in U.S. Pat. Nos. 2,656,508, 2,985,830 and 3,259,842, only a portion of which is shown, which portion includes a glass aperture tube 22 having a sensing aperture 24, which is disposed in a sample container 26, which sample container 26 contains a properly diluted blood sample 28 preferably of leukocytes or white blood cells (WBC), which cells or particles are suspended in an appropriate electrolyte solution, and when they are caused to be moved through said aperture 24, its effective impedance is changed with the passage of each particle therethrough, thereby causing the generation of a signal to be applied to a detector (not shown) suitably arranged to respond to such change for a fixed time interval, the counting time interval. Fluid, the diluted blood sample 28, is caused to be moved through the aperture 24 by reason of the fluid connection means 18 which is connected pressure-wise with the interior of the aperture tube 22, which includes a source of vacuum 30. This vacuum source 30 is connected at its upper end to both the interior of the aperture tube 22 through input tubing or conduit 32, which includes in its input line a one-way, input, valve 34, and to waste (not shown) through output tubing or conduit 36 which includes in its output line a one-way, output, valve 38.

The hemoglobin measuring apparatus 14 comprises an intake conduit 40, immersed at one end in the suspension 28 contained in the sample container 26 and connected at its other end to the input end of an optical measuring chamber or hemoglobin sample chamber 42, wherein hemoglobin (Hgb) concentrations can be measured by conventional photometric techniques. The output end of the hemoglobin sample chamber 42 is connected to the upper end of a syringe 44 through a hemoglobin overflow element 46 and an air filter 48 and choke 50. Both the air filter 48 and choke 50 are connected to an output line 52 including a one-way valve 54, choke 56 and an air filter 58.

The vacuum source 30 comprises a bellows or flexible means 60 having an upper and lower end 62 and 64, respectively, and a constant force means 66, a weight having a fixed value, having an upper and lower end 68 and 70, respectively, which upper end 68 is fixedly connected to the lower end 64 of the bellows means 60. The bellows or flexible means 60 has a valved chamber 72 that is contracted and expanded by "pumping" to force or draw suspension 28 in the sample container 26 and any air in the line 32 toward and through a nozzle 74 at its upper end; furthermore, said flexible means 60 of the preferred embodiment can be characterized as having axial flexibility and circumferential rigidity and having a low spring rate.

Figure 2:
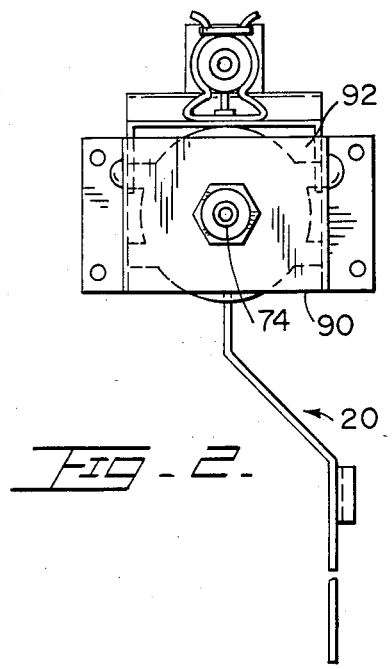
FIG. 2 is a top elevation view of the particle analyzing apparatus of FIG. 1.
Figure 3:
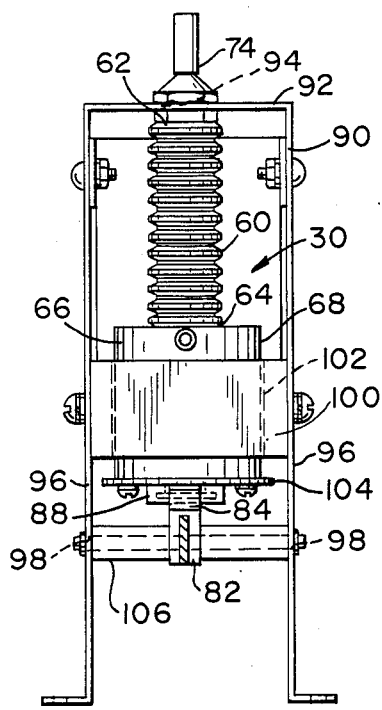
FIG. 3 is a front side elevation view of the particle analyzing apparatus of FIG. 2.
Figure 4:
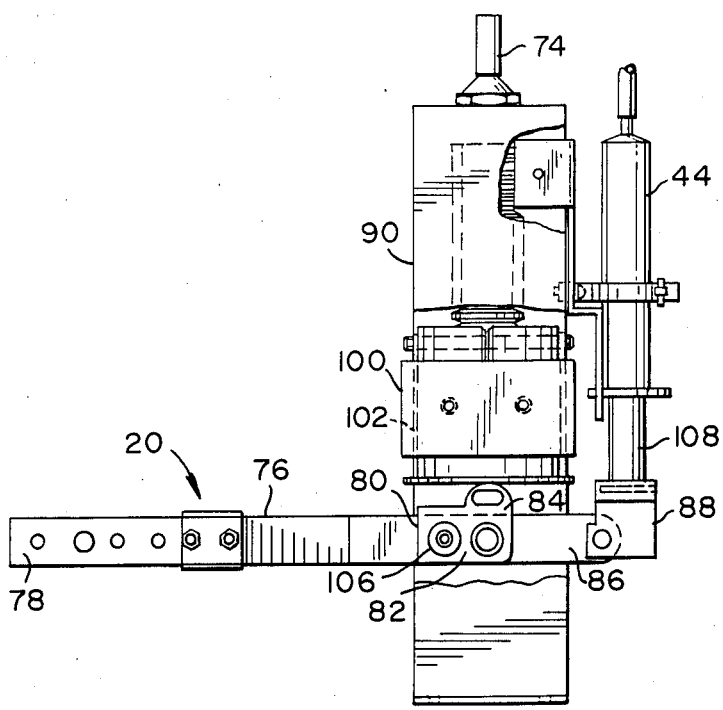
FIG. 4 is a front end elevation view of the particle analyzing apparatus of FIG. 2.

The actuation means 20, is coupled to the fluid connection means 18 at the lower end 70 of the constant force means 66, and functions to contract and then permits expansion of said bellows means 60. The actuation means 20 comprises an elongated lever member 76 having an actuation end 78, a fulcrum portion 80, a "pump" or vacuum plunger member 82 fixedly attached to said lever member 76 at its lower portion and has a semicircular upper portion 84 which is engageable with the bottom or lower end of the weight 66 and a syringe end 86 which is pivotably connected to a syringe adaptor 88. The actuation mean's lever 76 is set in either of two positions, a reset position or a count position. Referring more particularly to FIGS. 2-4, the vacuum source 30, syringe 44, and actuation means 20 are all connected to a common U-shaped housing 90, including an upper portion 92 having a centrally located opening 94 and two opposed side portions 96 each having opposed opening 98. The nozzle end 74 of the upper end 62 of the bellows 60 is threaded below its tip and its tip projects through the opening 94 and is fixedly fastened to the top and bottom of the upper portion 92 of the housing 90 by, preferably, top and bottom nuts secured to its threaded portion. The closed, lower end 64 of the bellows 60 includes a downwardly projecting tab having an opening within which a pin is inserted to connect the bellow's lower end 64 with the upper end 68 of the weight 66, which is slotted and within which such tab is disposed, which weight 66 is generally cylindrically shaped. A generally parallelepiped guide member 100 is fixedly secured at two of its opposed sides to the side portions 96 of the housing 90 and has a concentric opening 102 within which the weight 66 is disposed and guided. The bottom of the weight's lower end 70 has fixedly attached to it a disk 104 whose diameter is somewhat greater than the diameter of the guide member's opening 102. The lever 76 of the actuation means 20 is movably secured to a lower portion of the housing 90 by a rotatable pin assembly 106 which extends through openings in the fulcrum portion 80 of said lever 76, the lower portion of the pump plunger member 82, and the side portion's opposed openings 98. The syringe 44 is vertically clamped at its middle section to one of the side portions 96 of the housing 90 by a bracket and its lower movable plunger portion 108 is connected at its end to a slot within the movable syringe adaptor 88 which is pinned to the syringe end 86 of the lever 76.

Before operation can begin, the lever 76 is moved to the reset position and a sample 28 is placed in the sample container 26. The sample container 26 is positioned so that the WBC aperture 24 submerges itself in the sample 28. When the operator rapidly lifts the actuation end 78 of the lever 76 all the way up to the count position, the operative cycle begins with the weight 66 now free to fall by the force of gravity, but its rate of downward movement is slow because of the opposing force caused by moving the sample suspension 28 through the particle studying apparatus 10 as the sample suspension 28 is aspirated throught the aperture 24. The weight 66, as it is falling, generates a vacuum in the bellows 60, 6" of mercury in the preferred embodiment, which vacuum is substantially constant because the reactive spring forces of the bellows 60 are much smaller than the constant force of gravity operating on the weight 66 as it falls free since the bellow's material utilized has a very low spring rate. As the weight falls, the particles in suspension 28 are counted for a fixed time interval (which is less than the period of the operating cycle) by the particle counting device 16 as they enter its aperture 24. Also at the same time the operator lifts the lever 76, a vacuum is generated in the syringe 44. Some outside air is drawn into the hemoglobin measuring apparatus 14 of the particle studying apparatus 10 through the filter 58 and the adjustable valve 56 by the vacuum created by the syringe 44. Also because of the vacuum created by the syringe 44, some of the suspension 28 is aspirated into the tube 40 through the hemoglobin sample chamber 42 up to the hemoglobin overflow 46. The choke 50 is used to smooth the air flow in the hemoglobin line.

When the weight 66 has traveled downward a predetermined distance sufficient to provide a desired sample volume, and in the preferred embodiment a distance of 0.030 inches, the counting is completed. The weight 66 however continues to move downwards another 0.25 inches before coming to rest on the upper end 84 of the plunger 82 at which point the operative cycle is completed. The additional quarter inch is needed in case there is some air in the counting system which expands under the generated vacuum, causing the weight 66 to overtravel to complete the count. Air in the counting system does not result in a significant change in the magnitude of the vacuum. Once the operative cycle is completed, the lever 78 can be moved to the reset position which moves the weight 66 up thereby compressing the bellow 60 and forcing previously aspirated suspension liquid therein to pass through output valve 38 to waste. At the same time, the air is forced out of the hemoglobin sample chamber 42, through tube 40 in the particle suspension 28.

DETAILED DESCRIPTION OF AN ALTERNATIVE EMBODIMENT

Figure 5:
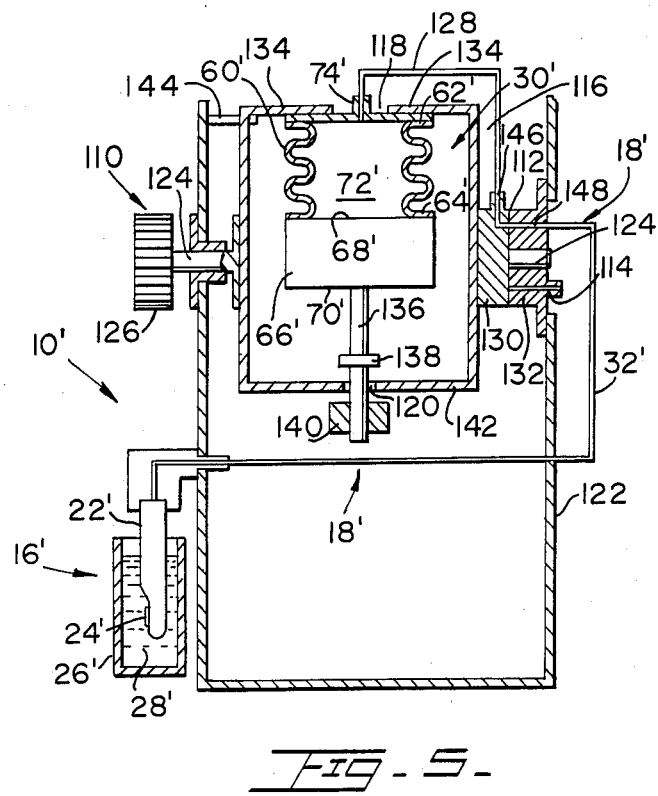
FIG. 5 is a partly cross-sectional and schematic view of a rotatable embodiment of the particle analyzing apparatus embodying the present invention.

Referring now to FIG. 5, wherein another, rotatable, embodiment of the invention is illustrated but without its hemoglobin measuring apparatus. A particle analyzing apparatus, generally indicated by reference numeral 10' comprises a particle counting device 16' wherein particles in suspension are caused to be moved through an aperture therein whose effective impedance is changed with the passage of each particle therethrough, which device is coupled to fluid connection means, generally indicated by reference numeral 18', for drawing a quantity of said suspension through said aperture, and actuation means, generally indicated by reference numeral 110, for operating said particle analyzing apparatuses 10'.

The particle counting device 16' comprises the conventional Coulter type apparatus such as previously described, only a portion of which is shown, which portion includes a glass aperture tube 22' having a sensing aperture 24', which is disposed in a sample container 26', which sample container 26' contains a properly diluted blood sample 28' preferably white blood cells (WBC), which cells or particles are suspended in an appropriate electrolyte solution, and when they are caused to be moved through said aperture 24', its effective impedance is changed with the passage of each particle therethrough, thereby causing the generation of a signal to be applied to a detector (not shown) suitably arranged to respond to such change. Fluid, the diluted blood sample 28', is caused to be moved through the aperture 24' by reason of the fluid connection means 18' which is connected pressure-wise with the interior of the aperture tube 22', and which includes a source of vacuum 30'. This vacuum source 30' is connected at its upper end to both the interior of the aperture tube 22' through input tubing or conduit 32', which includes in its input line a two-part, rotatable, control valve 112, and to waste (not shown) through an output passage 114 therein.

The vacuum source 30' comprises a bellows or flexible means 60' having an outer and inner end 62' and 64', respectively, and a constant force means 66, a weight having a fixed value, having a first and second end 68' and 70', respectively, which first end 68' is fixedly connected to the inner end 64' of the bellow means 60'. The bellows or flexible means 60' has a valved chamber 72' that is contracted and expanded by "pumping" to force or draw suspension 28' in the sample container 26' and any air in the line 32' toward and through a nozzle element 74' at its outer end; furthermore, said flexible means 60' of this alternative embodiment can also be characterized as having axial flexibility and circumferential rigidity and having a low spring rate.

The actuation means 110, is coupled to the fluid connection means 18' at the second end 70' of the constant force means 66' and at the outer end 62' of the bellows 60' and functions to contract and then permit expansion of said bellows means 60'.

The actuation means 110 comprises a rotatable, inner housing 116 having opposed first and second opening 118 and 120, respectively, and a stationary outer housing 122, to which the rotatable housing 116 is attached by a two-part shaft 124. One end of the shaft 124 has a manually operable knob 126 fixedly attached thereto and the other end of the shaft 124 is connected to the rotatable valve means 112. The rotatable valve 112 is connected through a section of conduit 128 to the nozzle element 74' of the bellows 60' and comprises an inner member 130 fixedly attached at its inner side to a side wall of the inner housing 116 and has its outer side fixedly attached to one end of said shaft 124 which shaft 124, is in turn rotatably attached to the valve's outer member 132, which is fixedly attached to a side wall of the outer housing 122. The nozzle element 74' of the upper end 62' of the bellows means 60' projects through the first opening 118 of the inner housing 116 and is fixedly fastened in a conventional manner to a first portion 134 of the housing 116. The closed, lower end 64' of the bellows 60' is fixedly attached, in a conventional manner to the weight's upper end 68'. A guiding rod member 136 fixedly attached to the second end 70' of said weight 66' and having a inner collar 138 and an outer, stroke control, collar 140 is slideably connected within opening 120 in a second portion 142 of said inner housing 116. The upper end of the outer housing 122 includes a stopper 144 fixedly attached thereto and disposed to permit the second portion 142 of the inner housing 116 to pass thereunder but which abuts a side wall at the end of the first portion 134 of said inner housing 116 to prevent rotation of said first portion 134 past said stopper 144 when the apparatus 10' is rotated into the count position.

The two-part, rotatable valve 112 has an L-shaped passage 146, in its inner member 130, which passage 146 connects into both an aperture passage 148 and the output passage 114 both formed in outer member 132, the L-shaped passage 146 connecting into the output passage 114 only when the inner housing 116 is rotated 180° from the position shown in FIG. 5. When the L-shaped passage 146 is in fluid communication with the aperture passage 148, the particle studying apparatus 10' is in its count position; when the inner housing 116 is rotated 180°, the apparatus 10' is in its reset position. The guiding rod member 136 maintains the bellows 60' in an axial positon at all times. The position of the inner collar 138 determines the stroke distance and the outer collar's weight can be adjusted to vary aspiration flow rate.

Before operation can begin, the knob 126 is quickly moved from the reset position to the count position after a sample 28' is placed in the sample container 26'. The sample container 26' is positioned so that the WBC aperture 24' submerges itself in the sample 28'. When the operator rotates the knob 76' all the way to the count position the operative cycle begins with the weight 66' now free to fall by the force of gravity, its rate of downward movement is slow because of the opposing force caused by moving the sample suspension 28' through the particle studying apparatus 10' as the sample suspension 28' is aspirated throught the aperture 24'. The weight 66' as it is falling generates a vacuum in the bellows 60', which vacuum is substantially constant because the reactive spring forces of the bellows 60' are much smaller than the constant force of gravity operating on the weight 66' as it falls free since the bellows material utilized has a very low spring rate. As the weight 66' begins to fall, the particles in suspension 28' are counted by the particle counting device 16' as they enter its aperture 24' for a fixed time interval.

When the weight 66' has traveled downward a predetermined distance sufficient to provide a desired sample volume, the count cycle is completed. The weight 66' however continues to move downwards another incremental amount before its collar 138 abutts against the inner wall surface of the second portion 142 of the inner housing 116; at this point the operative cycle is complete. Once the operative cycle is completed, the knob 128 is rotated 180° to position the particle study apparatus 10' to the reset position which positions the weight 66' above and against the bellows 60' thereby compressing it and forcing previously aspirated suspension liquid therein to pass through output passage 114 to waste. The constant force means in this embodiment includes not only the weight 66' but the guiding rod member 136 and its two collars 138 and 140.

The operative parameters of the preferred embodiment are as follows:
- bellows free length—3.39"
- bellows inside diameter—0.69"
- bellows outside diameter—0.97"
- weight of bellows—3 to 4 grams
- bellows spring rate—8 oz./inch
- weight (66)—1.67 lbs.
- stroke for a ten second count—0.030 inches The bellows element per se, is preferably molded from low density polyethylene. Accordingly, the calculated force variation during the count portion of the stroke generated by the bellows 60 is 0.015 pounds and the percent vacuum variation during the count portion of the stroke is 0.9% (i.e. 6" of mercury at the beginning of the count to 5.95" at the end of the count, all at sea level).

This particle analyzing device is capable of providing a substantially constant vacuum during the period the particles in suspension are counted as they are drawn through the aperture and furthermore is self-regulating in that the magnitude of the vacuum is only a function of altitude. Such device also repeatedly moves the same volume of sample in the same counting interval at any given altitude and at any given stroke length. It can be used at any altitude where a force of gravity exists with a simple calibration and obviates the necessity of a separate optics viewer to observe any aperture blockage as well as not requiring a pressure indicator. Its simple design and manual operation obviate any non-operator power source and permit inexpensive manufacture and maintenance. Utilizing only the force of gravity as its driving force obviates a number of problems since such force is not affected by temperature, stretching, aging, breaking, etc. thereby achieving a high degree of repeatability. Problems of course associated with the utilization of toxic substances are completely eliminated. Since the vacuum source operates without any sliding contact, the problems associated with mechanical friction are totally eliminated, a major advantage when high repeatability over time is required.

It should be understood that this invention is not limited to the specific details of construction and arrangement herein illustrated and/or described and that changes and modifications may occur to one skilled in the art without departing from the spirit and scope of the invention. For example the bellows could be replaced by a piston-cylinder arrangement, i.e. expandable means, which could include a piston disposed in sliding engagement within a cylinder or chamber; the weight would be fixedly attached to the lower end of the piston so it could be released to freely drive said piston within said cylinder by the force of gravity.

What we claim is:
1. A particle analyzing apparatus comprising:
   a particle counting device wherein a suspension of particles is caused to be moved during a counting interval through an aperture, said aperture having an effective electrical impedance which is changed with the passage of each particle therethrough; and
   fluid connection means connected to said particle counting device for drawing a quantity of said suspension through said aperture for a time period, said fluid connection means including a source of vacuum for generating a substantially constant level of vacuum during said counting interval, said source of vacuum comprising:

bellows means having an axis of symmetry and an end, and constant force means connected to said end of said bellows means, said constant force means having a vertical axis of symmetry, whereby the same quantity of said suspension is drawn through said aperture during each counting interval.

2. The apparatus as recited in claim 1, wherein said bellows means has a low spring rate.

3. The apparatus as recited in claim 1, further including actuation means, connected to said fluid connection means, for permitting said said source of vacuum to generate vacuum by allowing said constant force means to move at least substantially freely under the force of gravity at least substantially the entirety of said time period that said vacuum is being generated, whereby sliding friction is at least substantially eliminated in said generating of said vacuum.

4. The apparatus as recited in claim 1, further including actuation means, connected to said fluid connection means, for permitting said source of vacuum to generate a vacuum only when said axis of symmetry of said bellows means is in at least a substantially vertical position.

5. The apparatus as recited in claim 1, further including actuation means, connected to said fluid connection means, for permitting said source of vacuum to generate said vacuum by releasing said constant force means only when said vertical axis of symmetry of said constant force means is at least in a substantially vertical position.

6. A particle analyzing apparatus comprising:

a particle counting device wherein particles in suspension are caused to be moved through an aperture, said aperture having an effective electrical impedance which is changed with the passage of each particle therethrough;

fluid connection means connected to said particle counting device for drawing a quantity of said suspension through said aperture, said fluid connection means including a source of vacuum for generating a substantially constant level of vacuum, said source of vacuum comprising:

bellows means having an end, and constant force means connected to said end of said bellows means; and actuation means, connected to aid fluid connection means, adapted and arranged for causing said constant force means to move said bellows means effective to provide that said substantially constant level of said vacuum is repeatably generated with high precision.

7. A particle analyzing apparatus comprising:

a particle counting device wherein particles in suspension are caused to be moved through an aperture, said aperture having an effective electrical impedance which is changed with the passage of each particle therethrough;

fluid connection means connected to said particle counting device for drawing a quantity of said suspension through said aperture for a time period, said fluid connection means including a source of vacuum for generating a substantially constant level of vacuum, said source of vacuum comprising:

bellows means having a reactive force, an axis of symmetry and an end, and constant force means connected to said end of said bellows means, said constant force means having a vertical axis of symmetry; and actuation means, connected to said fluid connection means, for causing said constant force means to move said bellows means effectively permitting said source of vacuum to generate said vacuum by allowing said constant force means to move at least substantially freely under the force of gravity during at least substantially the entirety of said time period that said vacuum is being generated, whereby sliding friction is at least substantially eliminated in said generating of said vacuum.

8. The apparatus as recited in claim 7, wherein said actuation means permits said source of vacuum to generate said vacuum by releasing said constant force means only when said vertical axis of symmetry of said constant force means is at least in a substantially vertical position.

9. The apparatus as recited in claim 7, wherein said actuation means permits said source of vacuum to generate a vacuum only when said axis of symmetry of said bellows means is in at least a substantially vertical position.

10. A particle analyzing apparatus comprising:

a particle counting device wherein particles in suspension are caused to be moved through an aperture, said aperture having an effective electrical impedance which is changed with the passage of each particle therethrough;

fluid connection means connected to said particle counting device for drawing a quantity of said suspension through said aperture, said fluid connection means including a source of vacuum for generating a vacuum, said source of vacuum comprising:

bellows means having an axis of symmetry and an end, and constant force means connected to said end of said bellows means, said constant force means having a vertical axis of symmetry; and actuation means, connected to said fluid connection means, for permitting said source of vacuum to generate said vacuum by releasing said constant force means only when said vertical axis of symmetry of said constant force means is in at least in a substantially vertical position.

* * * * *

UNITED STATES PATENT AND TRADEMARK OFFICE
CERTIFICATE OF CORRECTION

PATENT NO. : 4,631,483

DATED : Dec. 23, 1986

INVENTOR(S) : Oscar Proni and Bobby D. James

It is certified that error appears in the above—identified patent and that said Letters Patent is hereby corrected as shown below:

Column 9, line 17, after "gravity" should be --during--.

Signed and Sealed this

Twentieth Day of October, 1987

Attest:

DONALD J. QUIGG

*Attesting Officer*     *Commissioner of Patents and Trademarks*